United States Patent [19]

Rosenblatt et al.

[11] Patent Number: 5,093,233
[45] Date of Patent: * Mar. 3, 1992

[54] PTH ANTAGONISTS WITH POSITION 13 MODIFICATION

[75] Inventors: Michael Rosenblatt, Ardmore; Eliahu Roubini, Lensvale, both of Pa.; Michael Chorev, Jerusalem, Israel; Ruth F. Nutt, Green Lane, Pa.

[73] Assignee: Merck & Co., Inc., Rahway, N.J.

[ * ] Notice: The portion of the term of this patent subsequent to Feb. 11, 2009 has been disclaimed.

[21] Appl. No.: 514,394

[22] Filed: Apr. 25, 1990

[51] Int. Cl.$^5$ .................. G01N 33/567; A61K 37/02; C07K 7/10

[52] U.S. Cl. .................. 435/7.21; 435/7.23; 435/7.2; 435/4.0; 514/12; 530/324; 530/325; 930/DIG. 822; 930/DIG. 820

[58] Field of Search .................. 530/324, 325; 514/12; 435/7.21, 7.23, 7.2, 4; 930/DIG. 822, 820

[56] References Cited

PUBLICATIONS

Horiuchi et al., Science, vol. 238, pp. 1566–1568 (1987).

The Merck Manual, 11th Ed., (1966), pp. 452–453.

Primary Examiner—Lester L. Lee
Assistant Examiner—T. Wessendorf
Attorney, Agent, or Firm—Salvatore C. Mitri; Charles M. Caruso

[57] ABSTRACT

The present invention relates to the use of peptide hormone analogues as inhibitors of their respective naturally occurring peptide hormone. The structure of the peptide hormone analogues is exemplified by parathyroid hormone (PTH), wherein Lys$^{13}$ is substituted to increase the biological activity of the PTH analogues. Thus, there are disclosed peptides having the formulae:

PTH(7-34)NH$_2$;
[Tyr$^{34}$]PTH(7-34)NH$_2$;
[D-Trp$^{12}$, Tyr$^{34}$]PTH(7-34)NH$_2$;
[Nle$^{8,18}$, D-Trp$^{12}$, Tyr$^{34}$]PTH(7-34)NH$_2$;
[Nle$^{8,18}$, Tyr$^{34}$]PTH(7-34)NH$_2$;
desamino[Nle$^{8,18}$, D-Trp$^{12}$, Tyr$^{34}$]PTH(7-34)NH$_2$; and,
desamino[Nle$^{8,18}$, D-Trp$^{12}$, Tyr$^{34}$]PTH(8-34)NH$_2$ wherein Lys$^{13}$ is modified in the epsilon-amino acid group by N,N-diisobutyl or 3-phenylpropanoyl.

4 Claims, No Drawings

PTH ANTAGONISTS WITH POSITION 13 MODIFICATION

FIELD OF THE INVENTION

This invention relates to the use of peptide hormone analogues for inhibiting the naturally occurring hormone peptide in vivo and in vitro. These peptide hormone analogues when administered to a vertebrate, such as mammals, block the endrocrine activity of the peptide hormone or other analogous molecules.

BACKGROUND OF THE INVENTION

The peptide analogues of this invention are useful in treating various diseases caused by an excess of the naturally occurring peptide and in treating peptide dependent tumors. One example of this invention relates to the synthesis of parathyroid hormone analogues useful for inhibiting the action of parathyroid hormone both in vivo and in vitro.

Analysis of the relation of structure to hormonal function has provided important insights into the mechanism of action of peptide hormones. Each type of peptide hormone has an affinity for specific receptors to which it binds. Upon binding, the peptide hormone acts either directly or causes a change in the intracellular concentration of a second messenger molecule such as cyclic AMP, cyclic GMP, inositol or calcium ions. These second messenger molecules, in turn, cause changes in the metabolism or physiology of the cell. These changes in cell metabolism or physiology are directly or indirectly dependent upon the binding of the peptide hormone to its specific cell surface receptor. Therefore, if the cell surface receptor is blocked then the hormone effect is also blocked.

Peptide hormone analogues have long been known as a method through which the biochemistry of hormones can be studied and evaluated. Endocrinologists have long desired a method for producing a class of peptide hormone analogues which would allow the blocking of specific hormone receptors without activating a change in the second messenger molecules, thereby avoiding the hormone induced metabolic changes.

Rosenblatt et al., U.S. Pat. No. 4,423,037 and the publications referred to therein describe the structure of certain peptide hormone analogues and their binding to cell receptors. In particular, these publications describe the properties of parathyroid hormone analogues and their physiological properties.

Scientific efforts over a period of many years have sought to understand the interaction between peptide hormones and the cell surface receptor specific for each peptide hormone. One of the peptide hormones, parathyroid hormone, has been studied by using analogues of parathyroid hormone (PTH). One objective of these studies has been to understand the binding of the peptide hormone to the cell surface receptor such that an analogue could be constructed which would bind with the same or greater affinity than the naturally occurring hormone. This would enable the peptide hormone analogue of parathyroid hormone to be used to block the effect of the naturally occurring parathyroid hormone.

One of the major problems encountered in this search for a clinically and pharmacologically effective parathyroid hormone analogue was the problem of agonist activity. Agonist activity is the property of the peptide hormone or its analogue to stimulate the change in second messengers which brings about the physiological change associated with the naturally occurring hormone. Therefore, the problem to be solved was to create hormone analogues which would bind with high affinity to the appropriate hormone cell surface receptor but not stimulate a change in the second messenger concentration, that is, not act as hormone itself. These analogues could then be used in treating hormone related diseases.

It is, therefore a primary object of this invention to stabilize the bioactive conformation of PTH by a substitution at the Lys 13 position of PTH in order to enhance the biological activity of PTH analogues. Another object of the present invention is to provide novel PTH analogues. Another object of the present invention is to provide a method of inhibiting the action of PTH through the administration of novel PTH analogues. Still another object of the invention is to provide PTH analogues wherein amino acid modifications result in binding to all the surface receptor without activating the second messenger molecule. The above and other objects are accomplished by the present invention in the manner more fully described below.

SUMMARY OF THE INVENTION

The present invention provides peptides having the formula
PTH(7-34)NH$_2$, [Tyr$^{34}$]PTH(7-34)NH$_2$,
[D-Trp$^{12}$, Tyr$^{34}$]PTH(7-34)NH$_2$,
[Nle$^{8,18}$,D-Trp$^{12}$,Tyr$^{34}$]PTH(7-34)NH$_2$,
[Nle$^{8,18}$,Tyr$^{34}$]PTH(7-34)NH$_2$, desamino
[Nle$^{8,18}$,D-Trp$^{12}$,Tyr$^{34}$]PTH(7-34)NH$_2$, and desamino[Nle$^{8,18}$,D-Trp$^{12}$,Tyr$^{34}$]PTH(8-34)NH$_2$,
wherein Lys$^{13}$ is modified in the epsilon amino acid group by N,N-diisobutyl or 3-phenylpropanoyl. The PTH can be human parathyroid hormone (hPTH), bovine parathyroid hormone (bPTH) or rat parathyroid hormone (rPTH). The above-mentioned peptides can be used in a method of acting upon on a PTH receptor which comprises administering a therapeutically effective but non-toxic amount of such peptide to a mammal. Additionally, an in vitro bioassay of PTH, wherein a measured amount of such peptides inhibit binding of PTH to a PTH receptor in vitro is an aspect of the present invention. A pharmaceutical composition containing a pharmaceutically acceptable carrier and, dispersed therein, a therapeutically effective but non-toxic amount of such peptide is another feature of this invention.

DETAILED DESCRIPTION OF THE INVENTION

The PTH antagonist compounds of this invention are illustrated by peptides having the formula PTH(7-34)NH$_2$,[Tyr$^{34}$]PTH(7-34)NH$_2$, [D-Trp$^{12}$,Tyr$^{34}$]PTH(7-34)NH$_2$, [Nle$^{8,18}$,D-Trp$^{12}$,Tyr$^{34}$]PTH(7-34)NH$_2$, [Nle$^{8,18}$, Tyr$^{34}$]PTH(7-34)NH$_2$, desamino[Nle$^{8,18}$,D-Trp$^{12}$,Tyr$^{34}$]PTH(7-34)NH$_2$, and desamino[Nle$^{8,18}$,D-Trp$^{12}$,Tyr$^{34}$] PTH(8-34)NH$_2$, wherein Lys 13 is modified in the epsilon-amino acid group by N,N-diisobutyl or 3-phenylpropanoyl. The PTH can be human parathyroid hormone (hPTH), bovine parathyroid hormone (bPTH) or rat parathyroid hormone (rPTH).

Representative examples of the peptide analogues of the present invention are desamino [Nle$^{8,18}$,D-Trp$^{12}$,Lys$^{13}$(N$^\epsilon$-CH$_2$)$_2$-Phenyl), Tyr$^{34}$]bPTH(7-34)NH$_2$, desamino[Nle$^{8,18}$,D-Trp$^{12}$, Lys$^{13}$(N$^\epsilon$-

CO(CH$_2$)$_2$-Phenyl),Tyr$^{34}$]bPTH(8-34) NH$_2$,[Nle$^{8,18}$,D-Trp$^{12}$, Lys$^{13}$(N$^\epsilon$-CO(CH$_2$)$_2$-Phenyl),Tyr$^{34}$]bPTH(7-34)NH$_2$, and [Nle$^{8,18}$,D-Trp$^{12}$,Lys$^{13}$(N$^\epsilon$,N$^\epsilon$-diisobutyl,-Tyr$^{34}$]bPTH(7-34)NH$_2$. These representative examples should not be construed as limiting the scope of this invention. Various other objects, features and advantages of the present invention will be more fully discussed from the following detailed description.

Extensive structure and activity studies have now led to the design of peptide hormone analogues which have high binding affinity for their respective cell surface receptors while not stimulating the production of second messenger molecules. Agonist activity is dependent upon the presence of the N-terminal amino acid sequence. The removal of two to six end terminal amino acids results in the loss of most if not all agonist activities. Therefore, the second messenger molecules are not affected by those analogues which have the altered amino terminus. PTH analogues with two to six amino acids removed from the N-terminus produces an inhibitor which still binds with high affinity to the peptide hormone receptor without causing a change in cyclic AMP concentration.

The following is the 34-amino acid sequence of bovine parathyroid hormone (bPTH):
H2N-Ala-Val-Ser-Glu-Ile-Gln-Phe-Met-His-Asn-Leu-Gly-Lys-His-Leu(15)-Ser-Ser-Met-Glu-Arg-Val-Glu-Trp-Leu-Arg-Lys-Lys-Leu-Gln-Asp(30)-Val-His-Asn-Phe-COOH.

The following is the 34-amino acid sequence of human parathyroid hormone (hPTH):
H2N-Ser-Val-Ser-Glu-Ile-Gln-Leu-Met-His-Asn(10)-Leu-Gly-Lys-His-Leu-Asn-Ser-Met-Glu-Arg(20)-Val-Glu-Trp-Leu-Arg-Lys-Lys-Leu-Gln-Asp(30)-Val-His-Asn-Phe-COOH.

The following is the 34 amino acid sequence of rat parathyroid hormone (rPTH):
H2N-Ala-Val-Ser-Glu-Ile-Gln-Leu-Met-His-Asn(10)-Leu-Gly-Lys-His-Leu-Ala-Ser-Val-Glu-Arg(20)-Met-Gln-Trp-Leu-Arg-Lys-Lys-Leu-Gln-Asp(30)-Val-His-Asn-Phe-COOH.

The peptide art designations contained herein are as follows: Ala, Alanine; Val, Valine; Ser, Serine; Glu, Glutamic Acid; Ile, Isoleucine; Gln, Glutamine; Phe, Phenylalanine; Met, Methionine; His, Histidine; Asn, Asparagine; Leu, Leucine; Gly, Glycine; Lys, Lysine; Trp, Tryptophan; Arg, Arginine; and Asp, Aspartic Acid. These standard abbreviations are well recognized in the art of peptide chemistry. It is also well recognized in the art that the chemical formula for -3-phenylpropanoyl is (N$^\epsilon$-CO(CH$_2$)$_2$-Phenyl.)

Fragments of peptide hormones containing the region specific for binding to the cell surface receptor can be used as inhibitors or blocking agents. For parathyroid hormone, the N-terminal 34 amino acids are sufficient to define binding specificity to the parathyroid hormone cell surface receptor. This receptor specificity is further defined by the following publications, herein incorporated by reference: M. Rosenblatt, et al., Endocrinology, 107:2, 545-550, 1980 and S. R. Nussbaum, et al., Journal of Biological Chemistry, 255:10183, 1980.

The present invention also provides a method of inhibiting the action of parathyroid hormone comprising the administration of therapeutically effective but non toxic amount of a parathyroid hormone analogue described above. The present invention also provides a method of treating osteoporosis or hypercalcemia comprising the administration of a therapeutically effective but non-toxic amount of a parathyroid hormone analogue described above. A method of treating hyperparathyroidism comprising the administration of a therapeutically effective but non-toxic amount of the parathyroid hormone analogues of this invention is also provided. A method of treating hyperparathyroidism expressed as a hypercalcemic crisis, renal failure or hypertension is also provided. A method of treating the disease state produced by a tumor or other cell overproducing a peptide hormone like molecule and method of treating immune diseases wherein the disease state comprises inflammation, an allergic response, or hyperactive lymphocytes is also provided by the novel peptide hormone analogues of the present invention.

The presence of D-amino acids in peptide hormone in place of L-amino acids results in a peptide resistant to catabolism. The insertion of tyrosine at position 34 in PTH results in a significant increase in the biological activity of the hormone in addition to increasing stability of the peptide. The utilization of D-amino acids in peptide hormone synthesis is described in the following publications herein incorporated by reference: Coltrera, et al., Biochemistry, 19:4380-4385, 1980; Rosenblatt et al., Biochemistry, 20:7246-7250, 1981.

The balance of the description will be divided into two sections. Section I will describe the preparation and structure of inhibitors of peptide hormone inhibitors. Section II will discuss the use of the peptide hormone inhibitors.

I. Preparation and Structure of Peptide Hormone Inhibitors

The technique of solid-phase peptide synthesis, developed by Merrifield "Solid-Phase Peptide Synthesis", Advances in Enzymology, 32:221-296, (1969) and G. Barany & R. B. Merrifield "Solid-Phase Peptide Synthesis", The Peptides Volume 2, editors E. Gross & J. Meienhofen (1980) has been successfully employed in the synthesis of peptide hormones including parathyroid hormone. This method is based on the strategy of having the carboxyl terminus of the peptide linked covalently to a solid support. The desired peptide sequence is prepared by stepwise coupling of single amino acids to a peptide chain growing from the carboxyl toward the amino terminus. Coupling is typically achieved by activation of the carboxyl group of the amino acid being attached to the resin, which may have other potentially reactive groups blocked. Following addition of an amino acid to the growing polypeptide chain, and prior to further chain elongation, the α-amino protecting (Boc) group is typically removed. Because each amino acid is coupled by nearly the same series of reactions, the need for elaborate strategies in the synthesis is minimized. Solubility is not a major issue during synthesis, because the peptide is linked to a solid support. This method is rapid and it can be utilized by a single worker. It is very convenient for the synthesis of multiple analogues with amino-terminal substitutions, because a single synthesis can be branched in multiple directions near the amino terminus, thereby creating many analogues varying only in the amino terminal region. In addition, modification of the ε-amino group of lysine can be achieved by the use of a unique protecting group (Fmoc) which can be selectively removed and then modified by a standard coupling cycle, omitting removal of the N-terminal Boc group.

II. Use of Peptide Hormone Inhibitors

The method of inhibiting the action of peptide hormones comprises the administration of a therapeutically effective but non-toxic amount of any Peptide hormone or analogue of the present invention. These hormone analogues retain specificity for the cell surface receptor without stimulating a physiological response. This method of use applies to the entire peptide hormone or its analogue, or to a fragment of the peptide hormone containing the receptor binding site.

The use of peptide hormone analogues is exemplified by parathyroid hormone analogues. The parathyroid hormone may be of bovine, human, rat, or any vertebrate origin. The analogue may contain all the amino acids except for the modified N-terminal region or it might contain the N terminal 7-34 amino acids. Individual amino acids can be substituted to improve biological or chemical stability.

The peptide hormone analogues of this invention can be used in vitro to measure the concentration of naturally occurring peptide hormone. This bioassay procedure is illustrated by a bioassay for parathyroid hormone. The unknown concentration of parathyroid hormone in a solution can be determined by measuring the amount of parathyroid hormone analogue required to inhibit its binding to the parathyroid hormone cell surface receptor. The concentration of PTH analogue required to block the action of parathyroid hormone is a direct indicator of the parathyroid hormone concentration.

Parathyroid hormone analogues can be used to diagnose the etiology of or to treat osteoporosis or hypercalcemia through the administration of a therapeutically effective but non-toxic amount of the parathyroid hormone analogues of this invention. Similarly, hyperparathyroidism and other aspects of hyperparathyroidism, such as a hypercalcemic crisis, renal failure or hypertension can be treated through the administration of the parathyroid hormone analogues of this invention.

Tumors and other aberrant cell growth often produce hormone-like substances causing a disease state. The use of peptide hormone analogues to block stimulation caused by such hormone-like substances can result in the alleviation of the disease state. Therefore, the peptide hormone analogues of the present invention can be administered to treat diseases caused by aberrant production of hormone-like substances.

Immune diseases such as inflammation, allergic responses and hyperactive lympocytes can be treated through the administration of peptide hormone analogues which block the action of peptide hormones, such as PTH analogues inhibiting the binding of PTH to cells of the immune system.

The peptide analogues of this invention exhibit both oral and parenteral activity and can be formulated in dosage forms for oral, parenteral, intra-nasal, or topical administration in a nontoxic but effective quantity, preferably dispersed in a pharmaceutically acceptable carrier. The dosage units of active ingredient in the pharmaceutical compositions of this invention may be varied; however, it is necessary that the amount of the active ingredient shall be such that a suitable dosage form is obtained. The selected dosage form depends upon the desired therapeutic effect, on the route of administration, and on the duration of treatment.

Solid dosage forms for oral administration include capsules, tablets, pills, powders and granules. In such solid dosage forms, the active compound is admixed with at least one inert diluent such as sucrose, lactose or starch. Such dosage forms can also contain, as is normal practice, additional substances other than inert diluent. In the case of capsules, tablets, and pills, the dosage forms may also contain buffering agents. Tablets and pills can additionally be prepared with an enteric coating.

Liquid dosage forms for oral administration include pharmaceutically acceptable emulsions, solutions, suspensions, syrups and elixers containing inert diluents commonly used in the pharmaceutical art. Besides inert diluents, such compositions can also include adjuvants, such as wetting agents, emulsifying and suspending agents, and sweetening agents. Preparations according to this invention for parenteral administration include sterile aqueous or non-aqueous solutions, suspensions or emulsions. Examples of such solutions, suspensions or emulsions are propylene glycol, polyethylene glycol, vegetable oils such as olive oil and injectable organic esters such as ethyloleate.

EXAMPLES

Examples provided are intended to assist in a further understanding of the invention. Particular materials employed, species and conditions, are intended to be further illustrative of the invention and not limitative of the reasonable scope thereof.

EXAMPLE 1

Hormone Analogues of PTH Synthesis and Purification of Peptide

Analogues of PTH were prepared by a modification of the solid-phase method of Merrifield. Syntheses were performed using an Applied Biosystems 430A Automated Peptide Synthesizer. 4-Methylbenzhydrylamine hydrochloride resin (polystyrene-1% by divinylbenzene, USB) was employed as the solid support in order to effect the carboxyamide ($CONH_2$) COOH-terminal modification.

The tertiary butyloxycarbonyl (Boc) group was used to protect the alpha amino group of each amino acid during coupling. Side-function protection was afforded as follows: (a) the hydroxyl group of serine was protected as the O-benzyl ether (BZL); (b) the hydroxyl group of tryosine as the 0-2,6-dichlorobenzyl ether (DCB) or p-bromobenzyloxycarbonyl ester (BrZ); (c) the carboxyl group of glutamic and aspartic acid as the benzyl (BZ) or cyclohexyl ester (Chx); (d) the imidazole nitrogen of histidine by the benzyloxymethyl (BOM) and the guanidine function of arginine was protected by the p-toluene-sulfonyl (TOS) group, and the indole imine by formyl groups (FOR); and (e) the lysine epsilon amino group by 2-chlorobenzylcarbonyl (ClZ) or Fluorenyl methyloxy carbonyl (Fmoc). All amino acids were obtained from Applied Biosystems, Inc., Peninsula Laboratories, or Bachem Chemicals.

The peptide-resin syntheses were carried out using Applied Biosystems, Inc. specified protocols. Double couplings were carried out for the incorporation of each amino acid. Deprotection times with trifluoroacetic acid were extended 6 minutes over manufacturer protocols. The substitution of the $\epsilon$-$NH_2$ of $Lys^{13}$ required the following modifications in the synthetic procedure described previously: 1. incorporation of the $N\alpha$-Boc-Lys($\epsilon$-Fmoc)-OH in position 13; and 2. $\epsilon$- amino Fmoc deprotection and modification of the free ε-NH₂ in Lys¹³.

Coupling of Boc-Lys(ε-Fmoc)-OH (0.94 g, 2.0 mmol) to the free amino terminus of [side chain protected Nle¹⁸,Tyr³⁴]bPTH(14-34)pMBHA-®(0.25 mmol) was carried out in the standard manner (1 mmol of preformed symmetrical anhydride). The recoupling of Boc-Lys(ε-Fmoc)-OH was performed in the presence of 5% diisopropylethylamine (DIPEA) in DMF and followed with consecutive washes; CH₂Cl₂ (1×1 minute) and DMF (1×1 minute).

Removal of ε-Fmoc protecting group was carried out in the standard manner. The protected resin-bound peptide was treated with 20% piperidine in DMF (1×1 minute followed by 1×20 minutes). The resin was consecutively washed with MeOH (1×1 minute), CH₂Cl₂ (4×1 minute) and DMF (2×1 minute). Acylation of ε-amino in Lys¹³ with 3-Phenylpropanoyl was carried out in the standard manner. Two consecutive couplings of DCC preformed 3-phenylpropionic anhydride (2 mmol each) to the ε-amino free side-chain protected resin-bound [Nle¹⁸,Tyr³⁴]bPTH(13-34) were carried out and followed by a sequence of washes; CH₂Cl₂ (1×1 minute), DMF (1×1 minute), MeOH (1×1 minute), CH₂Cl₂ (1×1 minute) and MeOH (1×1 minute). Testing with ninhydrin indicated the completion of the reaction, which was then followed by further washings; CH₂Cl₂ (4×1 minute) and DMF (2×1 minute).

Reductive alkylation of ε-amino in Lys¹³ with isobutyraldehyde was carried out in the standard manner. The free ε-amino free side chain protected resin-bound [Nle¹⁸,Tyr³⁴]bPTH(13-34) was treated with isobutyraldehyde (0.072 mL, 1.25 mmol) in 1% AcOH/DMF (10 mL) followed by portionwise addition of NaCNBH₃ (79 mg, 1.25 mmol) over 40 minutes. After 1 hour the reaction mixture was filtered off and repeated with 20-fold excess of reagent which were allowed to react overnight. The resin was then washed in the following sequence; CH₂Cl₂ (3×1 minute), DMF (2×1 minute), MeOH (1×1 minute) (negative ninhydrin test), CH₂Cl₂ (4×1 minute), ethanol (2×1 minute), and DMF (2×1 minute).

The peptide was cleaved from the copolymer resin with simultaneous removal of the side-chain protecting groups similar to the 2 step HF cleavage procedure described by Tam, J.A.C.S. 105: 6442-6455 (1983). In the first HF step, the following ratios of reagents were used: 5% p-cresol, 5% p-thiocresol, 65% dimethyl sulfide and 25% HF. 10 ml of mixture per gram of peptide resin was used for 2 hours at 0° C. In the second HF step the following ratio of reagents were used: 5% p cresol, 5% p-thiocresol and 90% HF. The cleavage was carried out for 75 min. at 0° C. After removal of HF the peptide-resin mixture was washed with anhydrous ether to remove scavenger. The peptide was then extracted with 50% acetic acid and water. The washes were combined and chromatographed using Sephadex G-50F, eluting with 50% HOAc.

After lyophilization, the partially purified peptide was chromatographed by reverse phase HPLC (Vydac C₄ bonded silica, 15 u particle size, 300A pore size, using aqueous acetonitrile gradient 10-50% B for 200 min (A=5% ACN/95% H₂O, 0.1% TFA, B=100% Acetonitrile, 0.1% TFA,) at a flow rate of 100 ml/min and monitored at 214 nm). Fractions through the peak were analyzed by analytical reversed phase HPLC and the fractions containing a single peak were pooled and lyophilized.

EXAMPLE 2

PTH Binding Assay Results in Bovine Renal Membranes

PTH analogues were analyzed in a new receptor assay reported in Goldman et al., Endocrin. 123: 1468-1475 (1988). The binding assay used [Nle⁸,¹⁸,¹²⁵I-Tyr³⁴]bPTH (1-34)NH₂ which was purified by HPLC (Novapak C₁₈, 32-35% CH₃CN in 0.1% TFA) and was stored as aliquots in 25 mM TrisHCl/1%BSA at −70° C. Bovine renal cortical plasma membranes were incubated with radioligand (25,000 cpm) in a Tris-containing buffer (250 ul) for 30 min. at 21° C. Once equilibrium was reached, bound and free radioligand were separated by centrifugation. High specific binding (85%) to bovine renal cortical membranes was obtained consistently.

TABLE

| Structure | Binding $K_B$(nM) |
| --- | --- |
| 1) desamino[Nle⁸,¹⁸,D-Trp¹², Lys¹³(Nε—CO(CH₂)₂-Phenyl), Tyr³⁴]bPTH(7-34)NH₂ | 13 ± 2 |
| 2) desamino[Nle⁸,¹⁸,D-Trp¹², Lys¹³(Nε—CO(CH₂)₂-Phenyl), Tyr³⁴]bPTH(8-34)NH₂ | 4 ± 1 |
| 3) [Nle⁸,¹⁸,D-Trp¹²,Lys¹³ (Nε—CO(CH₂)₂-Phenyl),Tyr³⁴] bPTH(7-34)NH₂ | 4 ± 1 |
| 4) [Nle⁸,¹⁸,D-Trp¹²,Lys¹³ (Nε,Nε-diisobutyl),Tyr³⁴] bPTH(7-34)NH₂ | 35 ± 4 |

EXAMPLE 3

ROS 17/2.8 Adenylate Cyclase Assay Results

PTH analogues were analyzed in a rat osteosarcoma cell line (Ros 17/2.8) for their ability to inhibit cyclic AMP stimulation by 1nM [Nle⁸,¹⁸,Tyr³⁴]bPTH(1-34)NH₂ by the method described in R. J. Majeska et al., Endocrinol. 107, 1494 (1980). Cells, preloaded with [³H] adenine, were incubated with the agonist PTH(1-34) in the presence or absence of the PTH analogue for 5 minutes at 37° C. in the presence of IBMX (phosphodiesterase inhibitor). The formation of [³H] cAMP was followed to determine the effect of the PTH analogue.

| Structure | Adenylate Cyclase $K_I$(nM) |
| --- | --- |
| 3) [Nle⁸,¹⁸,D-Trp¹²,Lys¹³ (Nε—CO(CH₂)₂-Phenyl),Tyr³⁴] bPTH(7-34)NH₂ | 118.7 ± 21.5 |

EXAMPLE 4

Bovine Renal Membrane Adenylate Cyclase

PTH analogues were evaluated for their effects on the stimulation of cyclic AMP production by bovine renal membranes stimulated with 3nM [Nle⁸,¹⁸,Tyr³⁴]bPTH (1-34)NH₂. Bovine renal membranes were incubated with agonist in the presence or absence of the PTH analogue at 30° C. for 30 min. Cyclic AMP produced was measured as described (B. L. Brown et. al., Adv. Cyclic Neucleotide Res. 2, 24 (1972)).

| Structure | Adenylate Cyclase $K_I$(nM) |
|---|---|
| 1) desamino[Nle$^{8,18}$,D-Trp$^{12}$, Lys$^{13}$(N$^\epsilon$—CO(CH$_2$)$_2$-Phenyl), Tyr$^{34}$]bPTH(7-34)NH$_2$ | 138 ± 27 |
| 2) desamino[Nle$^{8,18}$,D-Trp$^{12}$, Lys$^{13}$(N$^\epsilon$—CO(CH$_2$)$_2$-Phenyl), Tyr$^{34}$]bPTH(8-34)NH$_2$ | 73 ± 22 |
| 3) [Nle$^{8,18}$,D-Trp$^{12}$,Lys$^{13}$ (N$^\epsilon$—CO(CH$_2$)$_2$-Phenyl),Tyr$^{34}$] bPTH(7-34)NH$_2$ | 57 ± 11 |
| 4) [Nle$^{8,18}$,D-Trp$^{12}$,Lys$^{13}$ (N$^\epsilon$,N$^\epsilon$-diisobutyl),Tyr$^{34}$] bPTH(7-34)NH$_2$ | 231 ± 23 |

EXAMPLE 5

B 10 Adenylate Cyclase Assay Results

PTH analogues were analyzed in a human osteosarcoma cell line, B 10, for the ability to inhibit cAMP stimulation by InM [Nle$^{8,18}$,Tyr$^{34}$]bPTH (1-34) NH$_2$ by the method described by R. J. Majeska et al., Endocrinol, 107, 1494 (1980).

| Structure | Binding $K_B$(nM) |
|---|---|
| 1) desamino[Nle$^{8,18}$,D-Trp$^{12}$, Lys$^{13}$(N$^\epsilon$—CO(CH$_2$)$_2$-Phenyl), Tyr$^{34}$]bPTH(7-34)NH$_2$ | 5.3 ± 0.9 |
| 2) desamino[Nle$^{8,18}$,D-Trp$^{12}$, Lys$^{13}$(N$^\epsilon$—CO(CH$_2$)$_2$-Phenyl), Tyr$^{34}$]bPTH(8-34)NH$_2$ | 3.5 ± 0.4 |
| 3) [Nle$^{8,18}$,D-Trp$^{12}$,Lys$^{13}$ (N$^\epsilon$—CO(CH$_2$)$_2$-Phenyl),Tyr$^{34}$] bPTH(7-34)NH$_2$ | 7.1 ± 0.2 |
| 4) [Nle$^{8,18}$,D-Trp$^{12}$,Lys$^{13}$ (N$^\epsilon$,N$^\epsilon$-diisobutyl),Tyr$^{34}$] bPTH(7-34)NH$_2$ | 15.9 |

With regard to Example 5 above, Majeska, et al., on page 1495 describe the andenylate cyclase assay as follows:

Adenylate cyclase assay
Confluent cultures were rinsed in CMFH and scraped into 0.5-1.0 ml buffer (10 mM Tris-HCl, pH 7.8; 1mM dithiothreitol, 0.2 mM MgCl$_2$; and 0.5 mM EGTA) and homogenized with 10 strokes of a Dounce homogenizer (pestle A). Adenylate cyclase activity was measured by the method of Salomon et al., (18) on samples of either homogenate or membrane pellets obtained by centrifugation of diluted homogenates at 47,000 × g for 30 minutes. The enzyme assay mix contained 0.1-0.3 mM [α-$^{32}$P]ATP, MgCl$_2$, and guanine nucleotides, as specified in the tables and figures, and 1 mM cAMP, 5 mM phosphocreatine, and 100 U/ml creatine phosphokinase.

Purified bovine PTH-(1-84), generously provided by Drs. H. Keutmann and M. Rosenblatt, Massachusetts General Hospital, Boston, Mass., was dissolved and diluted in 1.5 ml/liter acetic acid containing 1 g/liter bovine serum albumin (Pentex fraction V, Miles Laboratories, Elkhart, Ind.). L-Isoproterenol bitarate (Sigma Chemical Co., St. Louis, Mo.) was prepared immediately before use and dissolved and diluted in assay buffer, Control tubes were assayed in the presence of diluent alone.

What is claimed is:

1. A peptide selected from the group consisting of PTH(7-34)NH$_2$, [Tyr$^{34}$]PTH(7-34)NH$_2$, [D-Trp$^{12}$,Tyr$^{34}$]PTH(7-34)NH$_2$, [Nle$^{8,18}$,D-Trp$^{12}$,Tyr$^{34}$]PTH(7-34)NH$_2$, and [Nle$^{8,18}$,Tyr$^{34}$]PTH(7-34)NH$_2$, desamino [Nle$^{8,18}$,D-Trp$^{12}$,Tyr$^{34}$]PTH(7-34)NH$_2$, and desamino[Nle$^{8,18}$,D-Trp$^{12}$,Tyr$^{34}$]PTH (8-34)NH$_2$, wherein Lys$^{13}$ is modified in the epsilon-amino acid group by N,N-diisobutyl or 3-phenylpropanoyl and wherein said PTH can be hPTH, bPTH, or rPTH.

2. The peptide of claim 1, which is desamino[Nle$^{8,18}$,D-Trp$^{12}$, Lys$^{13}$ (N$^\epsilon$-CO(CH$_2$)$_2$-Phenyl),Tyr$^{34}$]bPTH(7-34)NH$_2$, desamino[Nle$^{8,18}$,D-Trp$^{12}$,Lys$^{13}$ (N$^\epsilon$-CO(CH$_2$)$_2$-Phenyl),Tyr$^{34}$]bPTH(8-34)NH$_2$, [Nle$^{8,18}$,D-Trp$^{12}$,Lys$^{13}$ (N$^\epsilon$-CO(CH$_2$)$_2$-Phenyl),Tyr$^{34}$]bPTH(7-34)NH$_2$, or [Nle$^{8,18}$,D-Trp$^{12}$,Lys$^{13}$ (N$^\epsilon$,N$^\epsilon$-diisobutyl),Tyr$^{34}$]bPTH(7-34)NH$_2$.

3. A pharmaceutical composition having PTH antagonist activity, comprising a pharmaceutically acceptable carrier and, dispersed therein, a therapeutically effective but nontoxic amount of a peptide of claim 1.

4. An in vitro bioassay of PTH, wherein radiolabeled PTH together with an effective amount of the peptide of claim 1 reacts with a PTH receptor, present in animal cells or membranes, and following the reaction, the amount of radiolabeled PTH bound to the receptor is measured.

* * * * *